(12) United States Patent
Sikkema et al.

(10) Patent No.: US 7,851,584 B2
(45) Date of Patent: *Dec. 14, 2010

(54) PROCESS FOR PREPARING MONOMER COMPLEXES

(75) Inventors: Doetze Jakob Sikkema, Wageningen (NL); David J Rodini, Midlothian, VA (US); Hasan Dindi, Wilmington, DE (US); James Arnold Schultz, Woolwich Township, NJ (US); Georg Valentin Martin, Langenfeld (DE); Ralf Demuth, Houston, TX (US); Michael Schelhaas, Cologne (DE)

(73) Assignees: E. I. du Pont de Nemours and Company, Wilmington, DE (US); Magellan Systems International, LLC, Richmond, VA (US)

( * ) Notice: Subject to any disclaimer, the term of this patent is extended or adjusted under 35 U.S.C. 154(b) by 265 days.

This patent is subject to a terminal disclaimer.

(21) Appl. No.: 11/909,923

(22) PCT Filed: Mar. 27, 2006

(86) PCT No.: PCT/US2006/011262

§ 371 (c)(1),
(2), (4) Date: Jul. 11, 2008

(87) PCT Pub. No.: WO2006/105076

PCT Pub. Date: Oct. 5, 2006

(65) Prior Publication Data

US 2009/0215946 A1 Aug. 27, 2009

Related U.S. Application Data

(60) Provisional application No. 60/665,776, filed on Mar. 28, 2005.

(51) Int. Cl.
C08G 73/06 (2006.01)
(52) U.S. Cl. ..................................... 528/423; 526/265
(58) Field of Classification Search ................. 528/423; 526/265
See application file for complete search history.

(56) References Cited

U.S. PATENT DOCUMENTS 3,227,793 A 1/1966 Cipiani ....................... 264/203

(Continued)

FOREIGN PATENT DOCUMENTS

EP 0 481 403 B1 5/1996

(Continued)

OTHER PUBLICATIONS

Gerber, A.H., "Thermally stable polymers derived from 2,3,5,6-tetraaminopyridine," J. of Polymer Science, 1973, 11, 1703-1719.

(Continued)

Primary Examiner—Randy Gulakowski
Assistant Examiner—Shane Fang
(74) Attorney, Agent, or Firm—Woodcock Washburn LLP

(57) ABSTRACT

Disclosed are processes for preparing monomer complexes that include contacting 2,3,5,6-tetraminopyridine free base in water with 2,5-dihydroxy terephthalic acid dipotassium salt to form an aqueous mixture, and adjusting the pH of the aqueous mixture to within the range of from about (3) to about (5) to precipitate the monomer complex. Processes of polymerizing the monomer complexes, polyareneazoles, filaments and yarns are also disclosed.

13 Claims, 2 Drawing Sheets

U.S. PATENT DOCUMENTS

| | | | |
|---|---|---|---|
| 3,414,645 A | 12/1968 | Morgan, Jr. | 264/210 |
| 3,424,720 A | 1/1969 | Rudner et al. | 260/47 |
| 3,767,756 A | 10/1973 | Blades | 264/184 |
| 3,804,804 A | 4/1974 | Gerber et al. | 260/47 CP |
| 3,940,955 A | 3/1976 | Welsh | 68/20 |
| 3,996,321 A | 12/1976 | Weinberger | 264/40.3 |
| 4,002,679 A | 1/1977 | Arnold | 260/556 A |
| 4,070,431 A | 1/1978 | Lewis et al. | 264/180 |
| 4,078,034 A | 3/1978 | Lewis | 264/181 |
| 4,079,039 A | 3/1978 | Gerber | 260/47 CP |
| 4,298,565 A | 11/1981 | Yang | 264/181 |
| 4,452,971 A | 6/1984 | Choe et al. | 528/336 |
| 4,533,693 A | 8/1985 | Wolfe et al. | 524/417 |
| 4,703,103 A | 10/1987 | Wolfe et al. | 528/179 |
| 4,772,678 A | 9/1988 | Sybert et al. | 528/179 |
| 4,845,150 A | 7/1989 | Kovak et al. | 524/602 |
| 4,847,350 A | 7/1989 | Harris | 528/179 |
| 4,898,924 A | 2/1990 | Chenevey et al. | 528/183 |
| 4,939,235 A | 7/1990 | Harvey et al. | 528/337 |
| 4,963,428 A | 10/1990 | Harvey et al. | 428/220 |
| 5,041,522 A | 8/1991 | Dang et al. | 528/183 |
| 5,089,591 A | 2/1992 | Gregory et al. | 528/185 |
| 5,168,011 A | 12/1992 | Kovar et al. | 428/373 |
| 5,276,128 A | 1/1994 | Rosenberg et al. | 528/184 |
| 5,367,042 A | 11/1994 | Pierini et al. | 528/183 |
| 5,393,478 A | 2/1995 | Sen et al. | 264/203 |
| 5,429,787 A | 7/1995 | Im et al. | 264/344 |
| 5,525,638 A | 6/1996 | Sen et al. | 521/61 |
| 5,552,221 A | 9/1996 | So et al. | 428/373 |
| 5,667,743 A | 9/1997 | Tai et al. | 264/184 |
| 5,674,969 A | 10/1997 | Sikkema et al. | 528/183 |
| 5,772,942 A | 6/1998 | Teramoto et al. | 264/184 |
| 6,228,922 B1 | 5/2001 | Wang et al. | 542/413 |
| 2003/0083421 A1 | 5/2003 | Kumar et al. | 524/496 |
| 2004/0096734 A1* | 5/2004 | Calundann et al. | 429/137 |
| 2006/0019094 A1 | 1/2006 | Lee | 428/364 |

FOREIGN PATENT DOCUMENTS

| | | |
|---|---|---|
| EP | 0 834 608 B1 | 3/2002 |
| EP | 1 553 143 A1 | 7/2005 |
| GB | 1 361 840 | 7/1974 |
| JP | 06-240596 | 8/1994 |
| JP | 09-78349 | 3/1997 |
| WO | WO 91/02764 A1 | 3/1991 |
| WO | WO 94/12702 A1 | 6/1994 |
| WO | WO 96/20303 A1 | 7/1996 |
| WO | WO 99/27169 A1 | 6/1999 |
| WO | WO2004/003080 A1 | 1/2004 |
| WO | WO2004/003269 A1 | 1/2004 |
| WO | WO2004/024797 A1 | 2/2004 |
| WO | WO 2006/014718 A1 | 2/2006 |
| WO | WO2006/105076 A2 | 10/2006 |
| WO | WO2006/105225 A1 | 10/2006 |
| WO | WO2006/105226 A1 | 10/2006 |
| WO | WO2006/105231 A1 | 10/2006 |

OTHER PUBLICATIONS

Lammers, M., et al., "Mechanical properties and structural transitions in the new rigid-rod polymer fibre PIPD ('M5') during the manufacturing process," Elsevier Sci. Ltd., 1997, S0032-3861, 7 pages.

Sikkema, D.J., "Design, synthesis and properties of a novel rigid rod polymer, PIPD or 'M5': high modulus and tenacity fibers with substantial compressive strength," Polymer, 1998, 39(24), 5981-5986.

* cited by examiner

PROCESS FOR PREPARING MONOMER COMPLEXES

CROSS REFERENCE TO RELATED APPLICATIONS

This application is the National Stage of International Application No. PCT/US2006/011262, filed Mar. 27, 2006, which claims the benefit of U.S. Provisional Application Nos. 60/665,776, filed Mar. 28, 2005, the disclosure of which is incorporated herein by reference in it's entirety.

FIELD OF THE INVENTION

The present invention generally relates to monomer complexes, rigid-rod polymers and processes for the preparation of such polymers. In particular, the present invention relates to methods of preparing monomer complexes that are used to make high viscosity rigid-rod polymeric compositions that are suitable for spinning into filaments and yarns.

BACKGROUND OF THE INVENTION

Advances in polymer chemistry and technology over the last few decades have enabled the development of high-performance polymeric fibers. For example, liquid-crystalline polymer solutions of heterocyclic rigid-rod polymers can be formed into high strength fibers by spinning liquid-crystalline solutions into wet fibers, removing solvent to dry the fibers, and heat treating the dried fibers. Examples of high-performance polymeric fibers that include poly(p-phenylene benzobisthiazole) ("PBZT") and poly(p-phenylene-2,6-benzobisoxazole) ("PBO").

Fiber strength is typically correlated to one or more polymer parameters, including composition, molecular weight, intermolecular interactions, backbone, residual solvent or water, macromolecular orientation, and process history. For example, fiber strength typically increases with polymer length (i.e., molecular weight), polymer orientation, and the presence of strong attractive intermolecular interactions. As high molecular weight rigid-rod polymers are useful for forming polymer solutions ("dopes") from which fibers can be spun, increasing molecular weight typically results in increased fiber strength.

Molecular weights of rigid-rod polymers are typically monitored by, and correlated to, one or more dilute solution viscosity measurements. Accordingly, dilute solution measurements of the relative viscosity ("$V_{rel}$" or "$\eta_{rel}$" or "$n_{rel}$") and inherent viscosity ("$V_{inh}$" or "$\eta_{inh}$" or "$n_{inh}$") are typically used for monitoring polymer molecular weight. The relative and inherent viscosities of dilute polymer solutions are related according to the expression $$V_{inh} = \ln(V_{rel})/C,$$

where ln is the natural logarithm function and C is the concentration of the polymer solution. $V_{rel}$ is a unitless ratio, thus $V_{inh}$ is expressed in units of inverse concentration, typically as deciliters per gram ("dl/g").

Rigid-rod polymer fibers having strong hydrogen bonds between polymer chains, e.g., polypyridobisimidazoles, have been described in U.S. Pat. No. 5,674,969 to Sikkema et al. An example of a polypyridobisimidazole includes poly(1,4-(2,5-dihydroxy)phenylene-2,6-pyrido[2,3-d:5,6-d']bisimidazole), which can be prepared by the condensation polymerization of tetraminopyridine and 2,5-dihydroxyterephthalic acid in polyphosphoric acid. Sikkema describes that in making one- or two-dimensional objects, such as fibers, films, tapes, and the like, it is desired that polypyridobisimidazoles have a high molecular weight corresponding to a relative viscosity ("$V_{rel}$" or "$\eta_{rel}$") of at least about 3.5, preferably at least about 5, and more particularly equal to or higher than about 10, when measured at a polymer concentration of 0.25 g/dl in methane sulfonic acid at 25° C. Sikkema also discloses that very good fiber spinning results are obtained with poly [pyridobisimidazole-2,6-diyl(2,5-dihydroxy-p-phenylene)] having relative viscosities greater than about 12, and that relative viscosities of over 50 (corresponding to inherent viscosities greater than about 15.6 dl/g) can be achieved. Accordingly, further technical advances are needed to provide even higher molecular weight rigid-rod polymers, such as polypyridobisimidazoles, that are characterized as providing polymer solutions having even greater viscosities.

As described further herein, the polypyridobisimidazole class of rigid-rod polymers is a sub-genus of the polypyridazoles class of rigid-rod polymers, which is a sub-genus of the polyareneazole class of rigid-rod polymers. Accordingly, further technical advances are needed to provide even higher molecular weight polyareneazole rigid-rod polymers.

SUMMARY OF THE INVENTION

The present invention provides processes for preparing a polyareneazole polymer including contacting, in polyphosphoric acid, azole-forming monomers and from about 0.05 to about 0.9 weight percent, based on the total weight of the azole-forming monomers, iron metal powder, and reacting the azole-forming monomers to form the polyareneazole polymer.

In other aspects, the present invention provides processes for preparing a polyareneazole polymer including contacting, in polyphosphoric acid, azole-forming monomers and from about 0.05 to about 0.9 weight percent, based on the total weight of the azole-forming monomers, metal powder comprising vanadium metal, chromium metal, or any combination thereof, and reacting the azole-forming monomers to form the polyareneazole polymer.

In certain aspects, the present invention also provides processes for preparing a polyareneazole polymer, including contacting, in polyphosphoric acid, an azole-forming monomer complex and tin metal powder, the azole-forming monomer complex synthesized using a molar excess of a first azole-forming monomer and a second azole-forming monomer, the tin metal powder added in an amount of from about 0.05 to about 0.9 weight percent, based on the total amount of azole-forming monomer complex, and reacting the monomer complex to form the polyareneazole polymer.

In other aspects, the present invention provides processes for making monomer complexes comprising 2,3,5,6-tetramino pyridine and 2,5-dihydroxy terephthalic acid monomers, including the steps of contacting a 2,3,5,6-tetraminopyridine free base in water to a 2,5-dihydroxy terephthalic acid dipotassium salt to form an aqueous mixture, and adjusting the pH of the aqueous mixture to within the range of from about 3 to about 5 to precipitate the monomer complex.

In certain aspects, the present invention provides processes for making monomer complexes composed of 2,3,5,6-tetramino pyridine and 2,5-dihydroxy terephthalic acid monomers, including the steps of contacting a molar excess 2,3,5,6-tetraminopyridine free base in water with 2,5-dihydroxy terephthalic acid dipotassium salt to form an aqueous mixture, and adjusting the pH of the aqueous mixture to within the range of from about 3 to about 5 to precipitate the monomer complex.

In other aspects, the present invention provides for polyareneazole polymers that are characterized as forming polymer solutions having an inherent viscosity of at least about 22 dl/g at 30° C. at a polymer concentration of 0.05 g/dl in methane sulfonic acid.

In certain aspects, the present invention provides for filaments and multifilament yarns prepared from poly(1,4-(2,5-dihydroxy)phenylene-2,6-pyrido[2,3-d:5,6-d']bisimidazole) polymers that are characterized as providing a polymer solution having an inherent viscosity of at least about 22 dl/g at 30° C. at a polymer concentration of 0.05 g/dl in methane sulfonic acid.

In other aspects, the present invention further provides processes for preparing a poly(1,4-(2,5-dihydroxy)phenylene-2,6-pyrido[2,3-d:5,6-d']bisimidazole) polymer, including the steps of contacting a molar excess of a 2,3,5,6-tetramino pyridine free base in water to a 2,5-dihydroxy terephthalic acid salt to form an aqueous mixture, adjusting the pH of the aqueous mixture to within the range of from about 3 to about 5 to precipitate a monomer complex composed of 2,3,5,6-tetramino pyridine and 2,5-dihydroxy terephthalic acid monomers, contacting, in polyphosphoric acid, the monomer complex with metal powder, the metal powder added in an amount of from about 0.05 to about 0.9 weight percent, based on the total weight of the monomer complex, and polymerizing the monomer complex in polyphosphoric acid to form the polymer solution.

In certain aspects, the present invention provides for preparing a poly(1,4-(2,5-dihydroxy)phenylene-2,6-pyrido[2,3-d:5,6-d']bisimidazole) polymer, including the steps of contacting 2,3,5,6-tetramino pyridine free base in water with 2,5-dihydroxy terephthalic acid dipotassium salt to form an aqueous mixture, adjusting the pH of the aqueous mixture to within the range of from about 3 to about 5 to precipitate a monomer complex composed of 2,3,5,6-tetramino pyridine and 2,5-dihydroxy terephthalic acid monomers, contacting, in polyphosphoric acid, the monomer complex with metal powder, the metal powder added in an amount of from about 0.05 to about 0.9 weight percent, based on the total weight of the monomer complex, and polymerizing the monomer complex in polyphosphoric acid to form the polymer solution.

Other aspects of the present invention will be apparent to those skilled in the art in view of the detailed description and drawings of the invention as provided herein.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods, compositions, and devices disclosed. In the drawings.

DETAILED DESCRIPTION OF ILLUSTRATIVE EMBODIMENTS

Figure 1:
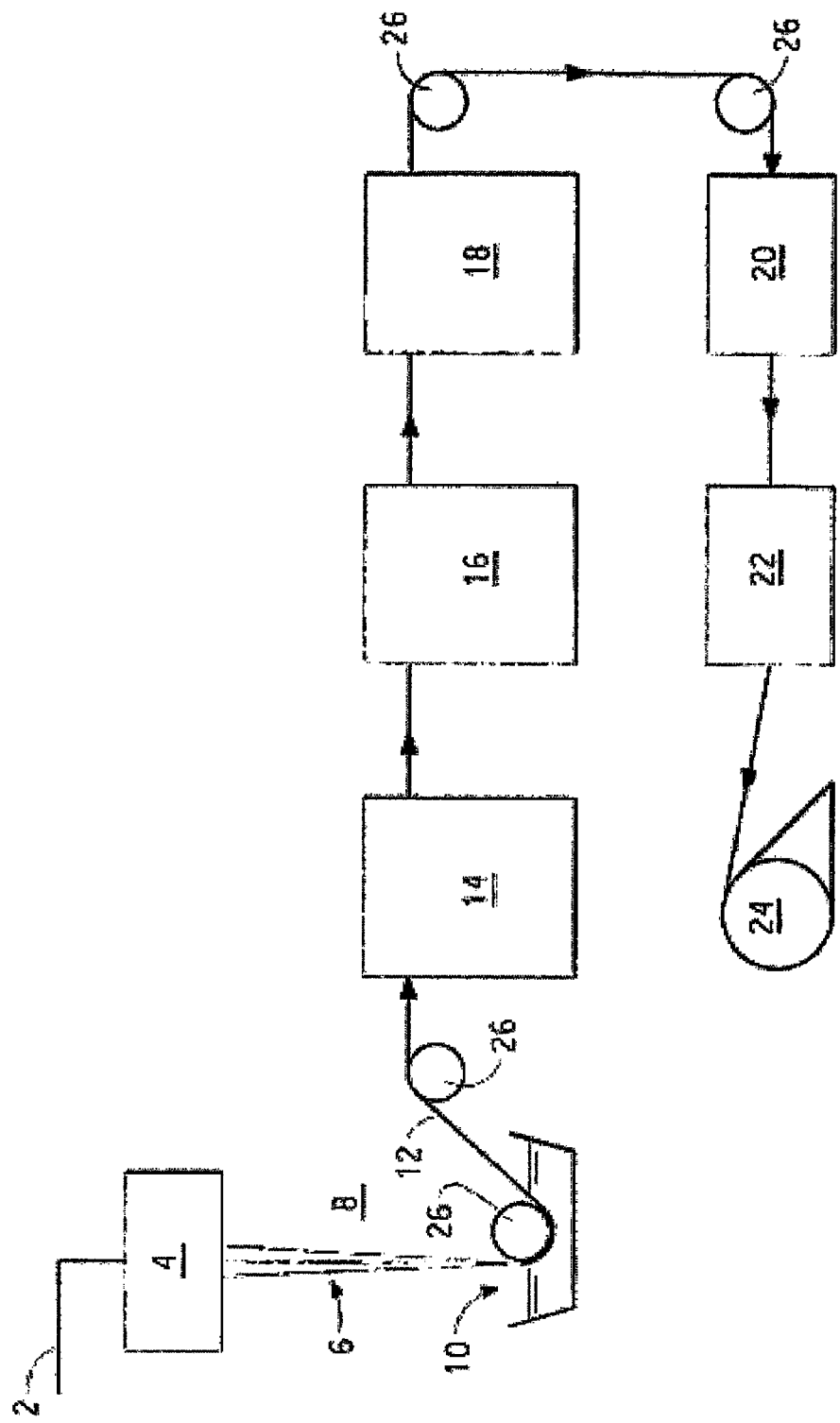
FIG. 1 is a schematic diagram of a polyareneazole fiber production process.

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. When any variable occurs more than one time in any constituent or in any formula, its definition in each occurrence is independent of its definition at every other occurrence. Combinations of substituents and/or variables are permissible only if such combinations result in stable compounds.

As employed above and throughout the disclosure, the following terms, unless otherwise indicated, shall be understood to have the following meanings.

Filaments of the present invention can be made from polyareneazole polymer. As defined herein, "polyareneazole" refers to polymers having either:

one heteroaromatic ring fused with an adjacent aromatic group (Ar) of repeating unit structure (a):

(a)

with N being a nitrogen atom and Z being a sulfur, oxygen, or NR group with R being hydrogen or a substituted or unsubstituted alkyl or aryl attached to N; or two hetero aromatic rings each fused to a common aromatic group (Ar¹) of either of the repeating unit structures (b1 or b2):

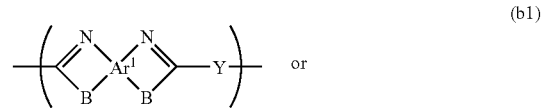

(b1)

or

(b2)

wherein N is a nitrogen atom and B is an oxygen, sulfur, or NR group, wherein R is hydrogen or a substituted or unsubstituted alkyl or aryl attached to N. The number of repeating unit structures represented by structures (a), (b1), and (b2) is not critical. Each polymer chain typically has from about 10 to about 25,000 repeating units. Polyareneazole polymers include polybenzazole polymers and/or polypyridazole polymers. In certain embodiments, the polybenzazole polymers comprise polybenzimidazole or polybenzobisimidazole polymers. In certain other embodiments, the polypyridazole polymers comprise polypyridobisimidazole or polypyridoimidazole polymers. In certain preferred embodiments, the polymers are of a polybenzobisimidazole or polypyridobisimidazole type.

In structure (b1) and (b2), Y is an aromatic, heteroaromatic, aliphatic group, or nil; preferably an aromatic group; more preferably a six-membered aromatic group of carbon atoms. Still more preferably, the six-membered aromatic group of carbon atoms (Y) has para-oriented linkages with two substituted hydroxyl groups; even more preferably 2,5-dihydroxy-para-phenylene.

In structures (a), (b1), or (b2), Ar and $Ar^1$ each represent any aromatic or heteroaromatic group. The aromatic or heteroaromatic group can be a fused or non-fused polycyclic system, but is preferably a single six-membered ring. More preferably, the Ar or $Ar^1$ group is preferably heteroaromatic, wherein a nitrogen atom is substituted for one of the carbon atoms of the ring system or Ar or $Ar^1$ may contain only carbon ring atoms. Still more preferably, the Ar or $Ar^1$ group is heteroaromatic.

As herein defined, "polybenzazole" refers to polyareneazole polymer having repeating structure (a), (b1), or (b2) wherein the Ar or $Ar^1$ group is a single six-membered aromatic ring of carbon atoms. Preferably, polybenzazoles include a class of rigid rod polybenzazoles having the structure (b1) or (b2); more preferably rigid rod polybenzazoles having the structure (b1) or (b2) with a six-membered carbocyclic aromatic ring $Ar^1$. Such preferred polybenzazoles include, but are not limited to polybenzimidazoles (B=NR), polybenzthiazoles (B=S), polybenzoxazoles (B=O), and mixtures or copolymers thereof. When the polybenzazole is a polybenzimidazole, preferably it is poly(benzo[1,2-d:4,5-d']bisimidazole-2,6-diyl-1,4-phenylene). When the polybenzazole is a polybenzthiazole, preferably it is poly(benzo[1,2-d:4,5-d']bisthiazole-2,6-diyl-1,4-phenylene). When the polybenzazole is a polybenzoxazole, preferably it is poly(benzo[1,2-d:4,5-d']bisoxazole-2,6-diyl-1,4-phenylene).

As herein defined, "polypyridazole" refers to polyareneazole polymer having repeating structure (a), (b1), or (b2) wherein the Ar or $Ar^1$ group is a single six-membered aromatic ring of five carbon atoms and one nitrogen atom. Preferably, these polypyridazoles include a class of rigid rod polypyridazoles having the structure (b1) or (b2), more preferably rigid rod polypyridazoles having the structure (b1) or (b2) with a six-membered heterocyclic aromatic ring $Ar^1$. Such more preferred polypyridazoles include, but are not limited to polypyridobisimidazole (B=NR), polypyridobisthiazole (B=S), polypyridobisoxazole (B=O), and mixtures or copolymers thereof. Yet more preferred, the polypyridazole is a polypyridobisimidazole (B=NR) of structure:

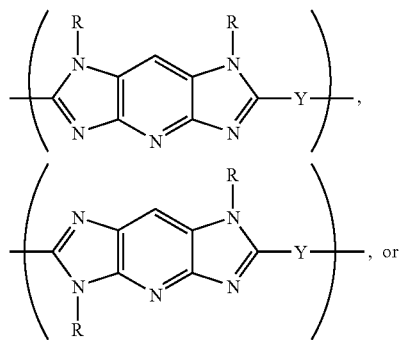

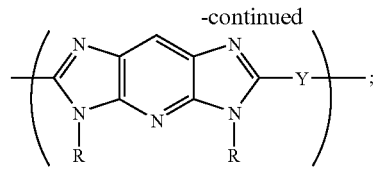

wherein N is a nitrogen atom and R is hydrogen or a substituted or unsubstituted alkyl or aryl attached to N, preferably wherein R is H. The average number of repeat units of the polymer chains is typically in the range of from about from about 10 to about 25,000, more typically in the range of from about 100 to 1,000, even more typically in the range of from about 125 to 500, and further typically in the range of from about 150 to 300.

As used herein, filaments of the present invention are prepared from polybenzazole (PBZ) or polypyridazole polymers. For purposes herein, the term "filament" or "fiber" refers to a relatively flexible, macroscopically homogeneous body having a high ratio of length to width across its cross-sectional area perpendicular to its length. The filament cross section may be any shape, but is typically circular.

As herein defined, "yarn" refers to a continuous length of two or more fibers, wherein fiber is as defined hereinabove.

For purposes herein, "fabric" refers to any woven, knitted, or non-woven structure. By "woven" is meant any fabric weave, such as, plain weave, crowfoot weave, basket weave, satin weave, twill weave, and the like. By "knitted" is meant a structure produced by interlooping or intermeshing one or more ends, fibers or multifilament yarns. By "non-woven" is meant a network of fibers, including unidirectional fibers, felt, and the like.

In some embodiments, the more preferred rigid rod polypyridazoles include, but are not limited to polypyridobisimidazole homopolymers and copolymers such as those described in U.S. Pat. No. 5,674,969 (to Sikkema, et al. on Oct. 7, 1997). One such exemplary polypyridobisimidazole is homopolymer poly(1,4-(2,5-dihydroxy) phenylene-2,6-diimidazo[4,5-b:4'5'-e]pyridinylene). This polymer is also known using various terminology, for example: poly(1,4-(2,5-dihydroxy)phenylene-2,6-pyrido[2,3-d:5,6-d']bisimidazole); poly[(1,4-dihydroxyimidazo[4,5-b:4',5'-e]pyridine-2,6-diyl) (2,5-dihydroxy-1,4-phenylene)]; poly[(2,6-diimidazo[4,5-b:4',5'-e]pyridinylene-(2,5-dihydroxy-1,4-phenylene)]; Chemical Abstracts Registry No. 167304-74-7, poly[(1,4-dihydrodiimidazo[4,5-b:4',5'-e]pyridine-2,6-diyl) (2,5-dihydroxy-1,4-phenylene)]; 2,5-dihydroxyterephthalic acid-1,2,4,5-tetraminopyridine copolymer; PIPD; pyridobisimidazole-2,6-diyl (2,5-dihydroxy-p-phenylene) copolymer; poly(1,4-(2,5-dihydroxy)phenylene-2,6-diimidazo[4,5-b:4',5'-e]pyridinylene); and poly(1,4-(2,5-dihydroxy)phenylene-2,6-pyrido[2,3-d5,6-d']bisimidazole).

The polyareneazole polymers used in this invention may have the properties associated with a rigid-rod structure, a semi-rigid-rod structure, or a flexible coil structure; preferably a rigid rod structure. When this class of rigid rod polymers has structure (b1) or (b2) it preferably has two azole groups fused to the aromatic group $Ar^1$.

Suitable polyareneazoles useful in this invention include homopolymers and copolymers. Up to as much as about 25 percent, by weight, of other polymeric material can be blended with the polyareneazole. Also copolymers may be used having as much as about 25 percent or more of other polyareneazole monomers or other monomers substituted for a monomer of the majority polyareneazole. Suitable polyareneazole homopolymers and copolymers can be made by known procedures, such as those described in U.S. Pat. Nos. 4,533,693 (to Wolfe et al. on Aug. 6, 1985), 4,703,103 (to Wolfe et al. on Oct. 27, 1987), 5,089,591 (to Gregory et al. on Feb. 18, 1992), 4,772,678 (Sybert et al. on Sep. 20, 1988), 4,847,350 (to Harris et al. on Aug. 11, 1992), 5,276,128 (to Rosenberg et al. on Jan. 4, 1994) and U.S. Pat. No. 5,674,969 (to Sikkema, et al. on Oct. 7, 1997), the entirety of each is incorporated by reference herein. Additives may also be incorporated in the polyareneazole in desired amounts, such as, for example, anti-oxidants, lubricants, ultra-violet screening agents, colorants and the like.

When any variable occurs more than one time in any constituent or in any formula, its definition in each occurrence is independent of its definition at every other occurrence. Combinations of substituents and/or variables are permissible only if such combinations result in stable compounds.

Several embodiments of the present invention are directed to polyareneazole filaments, more specifically to polybenzazole (PBZ) filaments or polypyridazole filaments, and processes for the preparation of such filaments. Other embodiments further include yarns, fabrics, and articles incorporating filaments of this invention, and processes for making such yarns, fabrics, and articles.

Filaments of the present invention are prepared from polybenzazole (PBZ) or polypyridazole polymers. For purposes herein, the term "filament" refers to a relatively flexible, macroscopically homogeneous body having a high ratio of length to width across its cross-sectional area perpendicular to its length. The filament cross section may be any shape, but is typically circular. Herein, the term "filament" is used interchangeably with the term "fiber".

Suitable polyareneazole monomers are reacted in a solution of non-oxidizing and dehydrating acid under non-oxidizing atmosphere with mixing at a temperature that is increased in step-wise or ramped fashion. The polyareneazole polymer can be rigid rod, semi-rigid rod or flexible coil. It is preferably a lyotropic liquid-crystalline polymer, which forms liquid-crystalline domains in solution when its concentration exceeds a critical concentration.

In certain embodiments of the present invention, there are provided processes for increasing the inherent viscosity of a polyareneazole polymer solution. These processes typically include the steps of contacting, in polyphosphoric acid, azole-forming monomers and iron metal powder, the iron metal powder added in an amount of from about 0.05 to about 0.9 weight percent, based on the total weight of the azole-forming monomers, and reacting the azole-forming monomers to form the polyareneazole polymer. The azole-forming monomers are suitably prepared separately in aqueous solutions and precipitated to form a monomer complex in a reaction vessel. For example, one suitable process uses a vessel under a nitrogen purge that is charged with a phosphoric acid buffer (pH in the range of from about 4.0 to about 4.5) and water. The solution is heated to approximately 50° C. In a second vessel under a nitrogen purge, an aqueous azole-forming monomer solution is made, preferably 2,5-dihydroxy terephthalic acid ("DHTA"), by combining an alkaline salt of 2,5-dihydroxy terephthalic acid, $Na_2S_2O_4$, $NH_4OH$, and water. In a third vessel, an aqueous mixture of a second azole-forming monomer that is capable of reacting with the first azole-forming monomer is prepared, preferably tetraminopyridine ("TAP")-3HCl—$H_2O$ solution is made by combining TAP-3HCl—$H_2O$ and water in a vessel under a nitrogen blanket, and then adding some $NH_4OH$.

The solution of the third vessel is transferred to the second vessel, and the pH is adjusted to within the range of from about 9 to about 10 in some embodiments. The combined solution is then warmed to approximately 50° C. while stirring with nitrogen bubbling until the solution clears. The cleared solution is transferred to the first vessel with enough additional $H_3PO_4$ to maintain the pH to about 4.5 during the addition process to precipitate the monomer complex to form a slurry. The slurry containing the monomer complex is typically filtered under nitrogen and washed with water and degassed ethanol. The monomer complex can be kept in an inert atmosphere and dried prior to polymerization.

A more preferred process for increasing the inherent viscosity of a polyareneazole polymer solution includes combining in an autoclave, 2,6-diamino-3,5-dinitropyridine ("DADNP"), water, 5% Pt/C catalyst and ammonium hydroxide and heating under pressure to hydrogenate the DADNP. After venting and cooling, activated carbon in water is added as a slurry to the autoclave and mixed. The solution is then filtered, forming a colorless TAP solution. This is added to a $K_2$-DHTA/$Na_2S_2O_4$ solution with mixing. A pre-mixed phosphate buffer solution is diluted with water and precharged in a coupling vessel and heated to about 50° C. while mixing. The basic TAP/$K_2$-DHTA mixture (pH about 10) is then added to the coupling vessel while adding aqueous $H_3PO_4$ to control the pH around 4.5. Large amounts of fine light-yellow monomer complex crystals form during the addition. The final pH is brought to about 4.5 while the monomer complex slurry is cooled. The slurry is then filtered to give a pale yellow cake. The monomer complex cake is washed with water followed by ethanol before being set to purge with nitrogen overnight. The color of the final cake is pale yellow.

Polymerization of the monomer complex is typically carried out in a reactor suitably equipped with connections for purging with inert gas, applying a vacuum, heating and stirring. Monomer complex, $P_2O_5$, PPA and powdered metal are typically added to the reactor. The reactor is typically purged, heated and mixed to effect polymerization. In one particularly preferred embodiment, about 20 parts of monomer complex, about 10 parts of $P_2O_5$, about 60 parts of polyphosphoric acid and about 0.1 parts tin or iron metal are added to a suitable reactor. The contents of the reactor are stirred at about 60 rpm and heated to about 100° C. for about one hour under vacuum with a slight nitrogen purge. The temperature is typically raised to at least 120° C., preferably to at least about 130° C., and preferably no more than about 140° C. for a few more hours, preferably about four hours. The temperature is then raised and held at a higher temperature, at least about 150° C., more typically at least about 170° C., and preferably at about 180° C. for about an hour, more preferably for about two hours. The reactor is typically flushed with nitrogen and a sample of the polymer solution is taken for viscosity determination.

The relative molecular weights of the polyareneazole polymers are suitably characterized by diluting the polymer products with a suitable solvent, such as methane sulfonic acid, to a polymer concentration of 0.05 g/dl, and measuring one or more dilute solution viscosity values at 30° C. Molecular weight development of polyareneazole polymers of the present invention is suitably monitored by, and correlated to, one or more dilute solution viscosity measurements. Accordingly, dilute solution measurements of the relative viscosity ("$V_{rel}$" or "$\eta_{rel}$" or "$n_{rel}$") and inherent viscosity ("$V_{inh}$" or "$\eta_{inh}$" or "$n_{inh}$") are typically used for monitoring polymer molecular weight. The relative and inherent viscosities of dilute polymer solutions are related according to the expression $$V_{inh}=\ln(V_{rel})/C,$$

where ln is the natural logarithm function and C is the concentration of the polymer solution. $V_{rel}$ is a unitless ratio of the polymer solution viscosity to that of the solvent free of polymer, thus $V_{inh}$ is expressed in units of inverse concentration, typically as deciliters per gram ("dl/g"). Accordingly, in certain aspects of the present invention the polyareneazole polymers are produced that are characterized as providing a polymer solution having an inherent viscosity of at least about 22 dl/g at 30° C. at a polymer concentration of 0.05 g/dl in methane sulfonic acid. Because the higher molecular weight polymers that result from the invention disclosed herein give rise to viscous polymer solutions, a concentration of about 0.05 g/dl polymer in methane sulfonic acid is useful for measuring inherent viscosities in a reasonable amount of time.

Various amounts and types of metal powders are useful for helping to build the molecular weight of polyareneazoles. In certain processes it is particularly preferred to use iron metal powder present in an amount of from about 0.1 to about 0.5 weight percent based on monomer. Suitable iron metal powder will be particularly fine to provide sufficient surface area for catalyzing the polymerization reaction. In this regard, iron metal powder will suitably have a particle size that will pass through a 200 mesh screen.

The azole-forming monomers suitably include 2,5-dimercapto-p-phenylene diamine, terephthalic acid, bis-(4-benzoic acid), oxy-bis-(4-benzoic acid), 2,5-dihydroxyterephthalic acid, isophthalic acid, 2,5-pyridodicarboxylic acid, 2,6-napthalenedicarboxylic acid, 2,6-quinolinedicarboxylic acid, 2,6-bis(4-carboxyphenyl) pyridobisimidazole, 2,3,5,6-tetraminopyridine, 4,6-diaminoresorcinol, 2,5-diaminohydroquinone, 1,4-diamino-2,5-dithiobenzene, or any combination thereof. Preferably, the azole-forming monomers include 2,3, 5,6-tetraminopyridine and 2,5-dihydroxyterephthalic acid. In certain embodiments, it is preferred that that the azole-forming monomers are phosphorylated. Preferably, phosphorylated azole-forming monomers are polymerized in the presence of polyphosphoric acid and a metal catalyst.

Azole-forming monomers can be selected for generating any of a number of polyareneazoles, and suitable polyareneazoles made according to certain embodiments of the processes of the present invention include polypyridoazoles, which preferably include polypyridobisimidazoles, which preferably include poly(1,4-(2,5-dihydroxy)phenylene-2,6-pyrido[2,3-d:5,6-d']bisimidazole).

Monomers are selected for generating any of a number of polyareneazoles, and suitable polyareneazoles made according to certain embodiments of the processes of the present invention will include a polybenzazole, which preferably includes a polybenzabisoxazole.

In several embodiments, the present invention also provides processes for increasing the inherent viscosity of a polyareneazole polymer. These processes suitably include the steps of contacting, in polyphosphoric acid, azole-forming monomers and a metal powder including vanadium metal, chromium metal, or any combination thereof, the metal powder added in an amount of from about 0.05 to about 0.9 weight percent, based on the total amount of azole-forming monomers, and reacting the monomers to form the polyareneazole polymer. Typically, these processes suitably form polyareneazoles that are characterized as providing a polymer solution having an inherent viscosity of at least about 22 dl/g at 30° C. at a polymer concentration of 0.05 g/dl in methane sulfonic acid. In certain embodiments, the metal powder is present in an amount of about 0.1 to about 0.5 weight percent based on monomer. Suitable metal powders have a fine particle size that provide a high surface area for effecting catalysis of the polymerization reaction. Accordingly, suitable metal powders have a particle size such that will pass through a 200 mesh screen. Similar monomers can be polymerized according to these processes to form polymers are provided using these processes as described above.

Several embodiments are also directed to processes for preparing a polyareneazole polymer that include contacting, in polyphosphoric acid, azole-forming monomer complex and tin metal powder, the azole-forming monomer complex synthesized using a molar excess of a first azole-forming monomer to a second azole-forming monomer, the tin metal powder added in an amount of from about 0.05 to about 0.9 weight percent, based on the total amount of azole-forming monomer complex, and reacting the monomer complex to form the polyareneazole polymer. Typically, these processes suitably form polyareneazoles that are characterized as providing a polymer solution having an inherent viscosity of at least about 22 dl/g at 30° C. at a polymer concentration of 0.05 g/dl in methane sulfonic acid. In certain embodiments, the metal powder is present in an amount of about 0.1 to about 0.5 weight percent based on monomer. Suitable metal powders have a fine particle size that provides a high surface area for effecting catalysis of the polymerization reaction. Accordingly, suitable metal powders have a particle size such that will pass through a 200 mesh screen. Similar monomers can be polymerized according to these processes to form polymers are provided using these processes as described above.

Processes for making a monomer complex comprising 2,3, 5,6-tetramino pyridine and 2,5-dihydroxy terephthalic acid monomers are also provided. In these embodiments, the processes typically include the steps of contacting a molar excess of a 2,3,5,6-tetraminopyridine free base in water to a 2,5-dihydroxy terephthalic acid dipotassium salt to form an aqueous mixture, and adjusting the pH of the aqueous mixture to within the range of from about 3 to about 5 to precipitate the monomer complex. More typically, in certain embodiments, the molar ratio of the 2,3,5,6-tetraminopyridine free base to the 2,5-dihydroxy terephthalic acid dipotassium salt is at least about 1.05 to 1, even more typically at least about 1.075 to 1, and particularly at least about 1.15 to 1.

The pH of the reaction mixtures are suitably maintained by adding an acid, preferably orthophosphoric acid, to the aqueous mixture. In various embodiments, suitable salts include an alkaline salt of the 2,5-dihydroxy terephthalic acid salt and an ammonium salt of 2,5-dihydroxy terephthalic acid. Preferably, the alkaline salt of the 2,5-dihydroxy terephthalic acid is 2,5-dihydroxy terephthalic acid dipotassium salt.

The pH of the aqueous mixture is typically adjusted to precipitate the monomer complex. A suitable pH for precipitating the monomer complex is in the range of from about 4.3 to about 4.6. After the monomer complex is formed, certain embodiments of the present invention also include one or more additional steps of polymerizing the monomer complex to form a polyareneazole. In these embodiments, any of the monomers as described herein can be used for forming any of the polyareneazole. For example, in certain embodiments, the polyareneazole, poly(1,4-(2,5-dihydroxy)phenylene-2,6-pyrido[2,3-d:5,6-d']bisimidazole), is formed using a monomer complex composed of 2,3,5,6-tetramino pyridine and 2,5-dihydroxy terephthalic acid monomers.

Several embodiments also provide processes for making a monomer complex composed of 2,3,5,6-tetramino pyridine and 2,5-dihydroxy terephthalic acid monomers. These processes include the steps of contacting 2,3,5,6-tetraminopyridine free base in water with 2,5-dihydroxy terephthalic acid dipotassium salt to form an aqueous mixture, and adjusting the pH of the aqueous mixture to within the range of from about 3 to about 5 to precipitate the monomer complex. In these embodiments, almost any molar ratio of the 2,3,5,6-tetraminopyridine free base to the 2,5-dihydroxy terephthalic acid dipotassium salt can be used, for example, a 1 to 1 molar ratio of 2,5-dihydroxy terephthalic acid sodium salt to a 2,3,5,6-tetraminopyridine free base can be used to prepare the complex. Typically, the molar ratio of the 2,3,5,6-tetraminopyridine free base to the 2,5-dihydroxy terephthalic acid dipotassium salt is at least about 1 to 1, more typically at least about 1.05 to 1, even more typically at least about 1.075 to 1, and further typically at least about 1.15 to 1. The pH is suitably adjusted by adding a dilute acid, preferably orthophosphoric acid, to the aqueous mixture. In certain preferred embodiments, the pH of the aqueous mixture is adjusted to within a range of from about 4.3 to about 4.6 to precipitate the monomer complex.

Poly(1,4-(2,5-dihydroxy)phenylene-2,6-pyrido[2,3-d:5,6-d']bisimidazole) polymers are also provided in several embodiments. These polymers are characterized as providing a polymer solution with methane sulfonic acid having an inherent viscosity of at least about 22 dl/g, more typically at least about 25 dl/g, even more typically at least about 28 dl/g, and further typically at least about 30 dl/g, at 30° C. at a polymer concentration of 0.05 g/dl. Various embodiments of the present invention also include filaments that can be prepared from these poly(1,4-(2,5-dihydroxy)phenylene-2,6-pyrido[2,3-d:5,6-d']bisimidazole) polymers. For example, polymer dope solutions can be extruded or spun through a die or spinneret to prepare or spin a dope filament. The spinneret preferably contains a plurality of holes. The number of holes in the spinneret and their arrangement is not critical to the invention, but it is desirable to maximize the number of holes for economic reasons. The spinneret can contain as many as 100 or 1000, or more, and they may be arranged in circles, grids, or in any other desired arrangement. The spinneret may be constructed out of any materials that will not be degraded by the dope solution. In various embodiments, multifilament yarns comprising a plurality of filaments are also provided. The number of filaments per multifilament yarn is approximately the number of holes in the spinneret. Typically, the multifilament yarns prepared with filaments of the present invention have a yarn tenacity of at least about 24 grams per denier ("gpd").

Additional processes for preparing poly(1,4-(2,5-dihydroxy)phenylene-2,6-pyrido[2,3-d:5,6-d']bisimidazole) polymers are also provided. These embodiments include contacting a molar excess of a 2,3,5,6-tetramino pyridine free base in water to a 2,5-dihydroxy terephthalic acid salt to form an aqueous mixture, adjusting the pH of the aqueous mixture to within the range of from about 3 to about 5 to precipitate a monomer complex composed of 2,3,5,6-tetramino pyridine and 2,5-dihydroxy terephthalic acid monomers, contacting, in polyphosphoric acid, the monomer complex with metal powder, the metal powder added in an amount of from about 0.05 to about 0.9 weight percent, based on the total weight of the monomer complex, and polymerizing the monomer complex in polyphosphoric acid to form the polymer solution. In certain of these embodiments, the molar ratio of 2,3,5,6-tetramino pyridine to 2,5-dihydroxy terephthalic acid typically is at least about 1.05 to 1, more typically at least about 1.075 to 1, and even more typically at least about 1.15 to 1. In certain of these embodiments, the pH is suitably adjusted by adding an acid, such as orthophosphoric acid, to the aqueous mixture. Suitably, the polyphosphoric acid has an equivalent $P_2O_5$ content after polymerization of typically at least about 81 percent, and more typically at least about 82 percent. The metal powder suitably includes iron powder, tin powder, vanadium powder, chromium powder, or any combination thereof. Preferably, the metal powder is iron powder. In certain of these embodiments, the 2,5-dihydroxy terephthalic acid salt is an alkaline salt or an ammonium salt of 2,5-dihydroxy terephthalic acid, and preferably the alkaline salt is 2,5-dihydroxy terephthalic acid dipotassium salt. In additional embodiments, the processes may further include one or more additional steps for preparing articles of manufacture, such as filaments and yarns. Thus, the present invention also provides the additional step of forming fibers from polymer solutions (i.e., dopes) of poly(1,4-(2,5-dihydroxy)phenylene-2,6-pyrido[2,3-d:5,6-d']bisimidazole) in polyphosphoric acid using one or fiber spinning processes. Preferably, poly(1,4-(2,5-dihydroxy)phenylene-2,6-pyrido[2,3-d:5,6-d']bisimidazole) polymer solutions have an inherent viscosity measured in 0.05 g/dl methane sulfonic acid of at least about 22 dl/g when measured in 0.05 g/dl methane sulfonic acid at 30° C.

There are also provided processes for preparing a poly(1,4-(2,5-dihydroxy)phenylene-2,6-pyrido[2,3-d:5,6-d']bisimidazole) that include the steps of contacting 2,3,5,6-tetramino pyridine free base in water with 2,5-dihydroxy terephthalic acid dipotassium salt to form an aqueous mixture, adjusting the pH of the aqueous mixture to within the range of from about 3 to about 5 to precipitate a monomer complex composed of 2,3,5,6-tetramino pyridine and 2,5-dihydroxy terephthalic acid monomers, contacting, in polyphosphoric acid, the monomer complex with metal powder, the metal powder added in an amount of from about 0.05 to about 0.9 weight percent, based on the total weight of the monomers, and polymerizing the monomers in polyphosphoric acid to form the polymer solution. In certain of these embodiments, the molar ratio of the 2,3,5,6-tetramino pyridine to the 2,5-dihydroxy terephthalic acid is typically at least about 1 to 1, more typically at least about 1.05 to 1, even more typically at least about 1.075 to 1, and further typically at least about 1.15 to 1. The pH is adjusted in certain of these embodiments by adding a suitable acid, preferably orthophosphoric acid, to the aqueous mixture. In certain embodiments, the reaction mixture preferably includes polyphosphoric acid having an equivalent $P_2O_5$ content of at least about 81 percent after polymerization, and more preferably at least about 82 percent after polymerization. In various embodiments, the metal powder typically includes iron powder, tin powder, vanadium powder, chromium powder, or any combination thereof. Preferably, the metal powder is iron powder. Certain embodiments further include at least one additional step of forming a fiber from the polymer solution. Suitable polymer solutions that are spinnable into filaments and multifilament yarn typically include poly(1,4-(2,5-dihydroxy)phenylene-2,6-pyrido[2,3-d:5,6-d']bisimidazole) having an inherent viscosity of at least about 22 dl/g when measured in 0.05 g/dl methane sulfonic acid at 30° C.

Certain embodiments of the present invention are discussed in reference to FIG. 1. In some embodiments, the polymer is formed in acid solvent providing the dope solution 2. In other embodiments, the polymer is dissolved in the acid solvent after formation. Either is within the ambit of the invention. Preferably the polymer is formed in acid solvent and provided for use in the invention. The dope solution 2, comprising polymer and polyphosphoric acid, typically contains a high enough concentration of polymer for the polymer to form an acceptable filament 6 after extrusion and coagulation. When the polymer is lyotropic liquid-crystalline, the concentration of polymer in the dope 2 is preferably high enough to provide a liquid-crystalline dope. The concentration of the polymer is preferably at least about 7 weight percent, more preferably at least about 10 weight percent and most preferably at least about 14 weight percent. The maximum concentration is typically selected primarily by practical factors, such as polymer solubility and dope viscosity. The concentration of polymer is preferably no more than 30 weight percent, and more preferably no more than about 20 weight percent.

The polymer dope solution 2 may contain additives such as anti-oxidants, lubricants, ultra-violet screening agents, colorants and the like which are commonly incorporated.

The polymer dope solution 2 is typically extruded or spun through a die or spinneret 4 to prepare or spin the dope filament 6. The spinneret 4 preferably contains a plurality of holes. The number of holes in the spinneret and their arrangement is not critical to the invention, but it is desirable to maximize the number of holes for economic reasons. The spinneret 4 can contain as many as 100 or 1000, or more, and they may be arranged in circles, grids, or in any other desired arrangement. The spinneret 4 may be constructed out of any materials that will not be degraded by the dope solution 2.

Fibers may be spun from solution using any number of processes, however, wet spinning and "air-gap" spinning are the best known. The general arrangement of the spinnerets and baths for these spinning processes is well known in the art, with the figures in U.S. Pat. Nos. 3,227,793; 3,414,645; 3,767,756; and 5,667,743 being illustrative of such spinning processes for high strength polymers, the entirety of each is incorporated by reference herein. In "air-gap" spinning the spinneret typically extrudes the fiber first into a gas, such as air. Using FIG. 1 to help illustrate a process employing "air-gap" spinning (also sometimes known as "dry-jet" wet spinning), dope solution 2 exiting the spinneret 4 enters a gap 8 (typically called an "air gap" although it need not contain air) between the spinneret 4 and a coagulation bath 10 for a very short duration of time. The gap 8 may contain any fluid that does not induce coagulation or react adversely with the dope, such as air, nitrogen, argon, helium, or carbon dioxide. The dope filament 6 is drawn across the air gap 8, with or without stretching and immediately introduced into a liquid coagulation bath. Alternately, the fiber may be "wet-spun". In wet spinning, the spinneret typically extrudes the fiber directly into the liquid of a coagulation bath and normally the spinneret is immersed or positioned beneath the surface of the coagulation bath. Either spinning process may be used to provide fibers for use in the processes of the invention. In some embodiments of the present invention, air-gap spinning is preferred.

The filament 6 is "coagulated" in the coagulation bath 10 containing water or a mixture of water and phosphoric acid, which removes enough of the polyphosphoric acid to prevent substantial stretching of the filament 6 during any subsequent processing. If multiple fibers are extruded simultaneously, they may be combined into a multifilament yarn before, during or after the coagulation step. The term "coagulation" as used herein does not necessarily imply that the dope filament 6 is a flowing liquid and changes into a solid phase. The dope filament 6 can be at a temperature low enough so that it is essentially non-flowing before entering the coagulation bath 10. However, the coagulation bath 10 does ensure or complete the coagulation of the filament, i.e., the conversion of the polymer from a dope solution 2 to a substantially solid polymer filament 12. The amount of solvent, i.e., polyphosphoric acid, removed during the coagulation step will depend on the residence time of the filament 6 in the coagulation bath, the temperature of the bath 10, and the concentration of solvent therein. For example, using a 20 weight percent solution of phosphoric acid at a temperature of about 23° C., a residence time of about one second will remove about 70 percent of the solvent present in the filament 6.

The residual polyphosphoric acid associated with the filament is typically substantially hydrolyzed and removed to preserve polymer fiber properties. PPA is conveniently hydrolyzed by heating the filament or yarn prior to washing and/or neutralization steps. One manner of hydrolysis includes convective heating of the coagulated fiber for a short period of time. As an alternative to convective heating, the hydrolysis may be effected by heating the wet, as coagulated filament or yarn in boiling water or an aqueous acid solution. This treatment provides PPA hydrolysis while adequately retaining the tensile strength of the product fiber. The heat treatment step may occur in a separate cabinet 14, or as an initial process sequence followed by one or more subsequent washing steps in an existing washing cabinet 14. In some embodiments, this is solved by (a) contacting the dope filament with a solution in bath or cabinet 14 thereby hydrolyzing PPA and then (b) contacting the filament with a neutralization solution in bath or cabinet 16 containing water and an effective amount of a base under conditions sufficient to neutralize sufficient quantities of the phosphoric acid, polyphosphoric acid, or any combination thereof in the filament.

After treatment to substantially hydrolyze PPA associated with the coagulated filament, hydrolyzed PPA may be removed from the filament or yarn 12 by washing in one or more washing steps to remove most of the residual acid solvent/and or hydrolyzed PPA from the filament or yarn 12. The washing of the filament or yarn 12 may be carried out by treating the filament or yarn 12 with a base, or with multiple washings where the treatment of the filament or yarn with base is preceded and/or followed by washings with water. The filament or yarn may also be treated subsequently with an acid to reduce the level of cations in the polymer. This sequence of washings may be carried out in a continuous process by running the filament through a series of baths and/or through one or more washing cabinets. FIG. 1 depicts one washing bath or cabinet 14. Washing cabinets typically comprise an enclosed cabinet containing one or more rolls which the filament travels around a number of times, and across, prior to exiting the cabinet. As the filament or yarn 12 travels around the roll, it is sprayed with a washing fluid. The washing fluid is continuously collected in the bottom of the cabinet and drained therefrom.

The temperature of the washing fluid(s) is preferably greater than 30° C. The washing fluid may also be applied in vapor form (steam), but is more conveniently used in liquid form. Preferably, a number of washing baths or cabinets are used. The residence time of the filament or yarn 12 in any one washing bath or cabinet 14 will depend on the desired concentration of residual phosphorus in the filament or yarn 12, but preferably the residence time are in the range of from about one second to less than about two minutes. In a continuous process, the duration of the entire washing process in the preferred multiple washing bath(s) and/or cabinet(s) is preferably no greater than about 10 minutes, more preferably more than about 5 seconds and no greater than about 160 seconds.

In some embodiments, preferred bases for the removal of hydrolyzed PPA include NaOH; KOH; $Na_2CO_3$; $NaHCO_3$;

$K_2CO_3$; $KHCO_3$; or trialkylamines, preferably tributylamine; or mixtures thereof. In one embodiment, the base is water soluble.

After treating the fiber with base, the process optionally may include the step of contacting the filament with a washing solution containing water or an acid to remove all or substantially all excess base. This washing solution can be applied in a washing bath or cabinet 18.

The fiber or yarn 12 may be dried in a dryer 20 to remove water and other liquids. The temperature in the dryer is typically about 80° C. to about 130° C. The dryer residence time is typically 5 seconds to perhaps as much as 5 minutes at lower temperatures. The dryer can be provided with a nitrogen or other non-reactive atmosphere. Then the fiber can optionally be further processed in, for instance, a heat setting device 22. Further processing may be done in a nitrogen purged tube furnace 22 for increasing tenacity and/or relieving the mechanical strain of the molecules in the filaments. Finally, the filament or yarn 12 is wound up into a package on a windup device 24. Rolls, pins, guides, and/or motorized devices 26 are suitably positioned to transport the filament or yarn through the process.

Preferably, the phosphorous content of the dried filaments after removal of the hydrolyzed PPA is less than about 5,000 ppm (0.5%) by weight, and more preferably, less than about 4,000 ppm (0.4%) by weight, and most preferably less than about 2,000 ppm (0.2%) by weight.

The invention is further directed, in part, to a yarn comprising a plurality of the filaments of the present invention, fabrics that include filaments or yarns of the present invention, and articles that include fabrics of the present invention. For purposes herein, "fabric" means any woven, knitted, or non-woven structure. By "woven" is meant any fabric weave, such as, plain weave, crowfoot weave, basket weave, satin weave, twill weave, and the like. By "knitted" is meant a structure produced by interlooping or intermeshing one or more ends, fibers or multifilament yarns. By "non-woven" is meant a network of fibers, including unidirectional fibers (if contained within a matrix resin), felt, and the like.

EXAMPLES

As used herein, the terms "mmole" and "millimole" are synonymous. All polymer solids concentrations, weight percents based on monomer, and polymer solution percent $P_2O_5$ concentrations are expressed on the basis of TD-complex as a 1:1 molar complex between TAP and DHTA. The TD-complex is believed to be a monohydrate.

The test methods described below were used in the following Examples.

Temperature: measured in degrees Celsius (° C.).

Denier: determined according to ASTM D 1577 and is the linear density of a fiber as expressed as weight in grams of 9000 meters of fiber.

Tenacity: determined according to ASTM D 3822 and is the maximum or breaking stress of a fiber as expressed as force per unit cross-sectional area.

Elemental Analysis: Elemental analysis of alkaline cation (M) and phosphorus (P) is determined according to the inductively coupled plasma (ICP) method as follows. A sample (1-2 grams), accurately weighed, is placed into a quartz vessel of a CEM Star 6 microwave system. Concentrated sulfuric acid (5 ml) is added and swirled to wet. A condenser is connected to the vessel and the sample is digested using the moderate char method. This method involves heating the sample to various temperatures up to about 260° C. to char the organic material. Aliquots of nitric acid are automatically added by the instrument at various stages of the digestion. The clear, liquid final digestate is cooled to room temperature and diluted to 50 ml with deionized water. The solution may be analyzed on a Perkin Elmer optima inductively coupled plasma device using the manufacturers' recommended conditions and settings. A total of twenty-six different elements may be analyzed at several different wavelengths per sample. A 1/10 dilution may be required for certain elements such as sodium and phosphorus. Calibration standards are from 1 to 10 ppm.

Many of the following examples are given to illustrate various embodiments of the invention and should not be interpreted as limiting it in any way. All parts and percentages are by weight unless otherwise indicated.

Monomer Complex Examples

Example 1

This example illustrates the use of 5 percent molar excess of 2,3,5,6-tetraminopyridine ("TAP") in the making of monomer complex by a batch process. Water was degassed and deionized.

A first stirred 2-liter resin kettle under a nitrogen purge was charged with 50 ml of 85% $H_3PO_4$ and 450 ml water, followed by the addition of a 10 percent by weight sodium hydroxide solution until the pH of the material in the kettle was approximately 4.6 as measured by a pH probe. The solution was heated to approximately 50° C.

In a second stirred 2-liter resin kettle under a nitrogen purge, a 2,5-dihydroxy terephthalic acid ("DHTA") solution was made by combining 41.1 g of a dipotassium salt of 2,5-dihydroxy terephthalic acid ("$K_2$-DHTA"), 1 g $Na_2S_2O_4$, 60 g $NH_4OH$, and 700 g water. The $K_2$-DHTA and $Na_2S_2O_4$ were weighed in a glove box first.

A TAP-3HCl—$H_2O$ solution was made by combining 700 g water and 42 g TAP-3HCl.$H_2O$ in a quart bottle equipped with a septum (under a nitrogen blanket). 60 g of $NH_4OH$ were then added. This solution was cannulated to the second resin kettle. This combined solution in the second kettle had a pH of approximately 9 to 10. The combined solution was warmed to approximately 50° C. while stirring with nitrogen bubbling until the solution became clear. This solution was cannulated to the first resin kettle along with enough additional $H_3PO_4$ to adjust the pH to 4.5 to precipitate the monomer complex to form a slurry. The $H_3PO_4$ solution was made by diluting 50 ml of 85% $H_3PO_4$ in 500 ml water.

The slurry containing the monomer complex was filtered under nitrogen and washed twice with 200 ml of water (6-8 grams water per gram of wet product slurry) and with 10 ml degassed ethanol (~1 gram ethanol per gram of wet product). The monomer complex was kept under nitrogen and dried by steam heating overnight, and recovered in a nitrogen atmosphere glove box.

Polymerization (Example With 5.0% molar excess TAP in Monomer Complex Formation). Into a clean dry 200 ml glass tubular reactor having an inside diameter of 4.8 cm and that was equipped with the necessary connections for purging nitrogen and applying a vacuum, and around which a heating jacket was arranged and which further contained double helix shaped basket stirrer were charged with 23.00 g of monomer complex, 11.24 g of $P_2O_5$, 66.29 g of polyphosphoric acid ("PPA") with a % $P_2O_5$ equivalent to 85.15%, and 0.115 g Sn. The contents were stirred at 60 rpm and heated to 100° C. for one hour under vacuum with a slight nitrogen purge. The temperature was raised and held at 137° C. for 4 hours. The temperature was raised and held at 180° C. for 2 hours. The reactor was flushed with nitrogen. a sample of the polymer solution was diluted with methane sulfonic acid to 0.05% concentration, and the inherent viscosity was measured at 30° C. to be $n_{inh}$=23 dl/g.

Example 2

The procedure of Example 1 was repeated, however 43 grams of TAP were used to make the TAP.3HCl.H$_2$O solution, providing a molar excess of 7.5% TAP as compared to a molar excess of 5% TAP as in Example 1.

Polymerization (Example With 7.5% molar excess TAP in Monomer Complex Formation). Into a clean dry 200 ml glass tubular reactor having an inside diameter of 4.8 cm, equipped with the necessary connections for purging nitrogen and applying a vacuum, and around which a heating jacket was arranged and which further contained double helix shaped basket stirrer, was charged 20.00 g of monomer complex, 7.78 g of P$_2$O$_5$, 59.52 g of PPA with a % P$_2$O$_5$ equivalent to 85.65%, and 0.115 g Sn. The stirrer was turned on at 100 rpm and the contents were heated to 100° C. for one hour under vacuum with a slight N$_2$ purge. The temperature was raised and held at 137° C. for 3 hours. The temperature was raised and held at 180° C. for 2 hours. The reactor was flushed with nitrogen gas ("N$_2$") and a sample of the polymer solution was diluted with methane sulfonic acid to 0.05% concentration. The $n_{inh}$=28.5 dl/g.

Example 3

The procedure of Example 1 was repeated, however 46 grams of TAP were used to make the TAP.3HCl.H$_2$O solution, providing a molar excess of 15% TAP compared to a 5% molar excess as in Example 1.

Polymerization (Example With 15% molar excess TAP in Monomer Complex Formation). Into a clean dry 200 ml glass tubular reactor having an inside diameter of 4.8 cm, equipped with the necessary connections for purging nitrogen and applying a vacuum, and around which a heating jacket was arranged and which further contained double helix shaped basket stirrer was charged 20.00 of monomer complex, 7.79 g of P$_2$O$_5$, 59.54 g of PPA with a P$_2$O$_5$ equivalent to 85.65%, and 0.115 g Sn. The contents were stirred at 100 rpm and heated to 100° C. for one hour under vacuum with a slight N$_2$ purge. The temperature was raised to 137° C. held there for 4 hours. The temperature was raised and held at 180° C. for 2 hours. The reactor was flushed with N$_2$ and a sample of the polymer solution was diluted with methane sulfonic acid to 0.05% concentration. The $n_{inh}$=33.4 dl/g.

Example 4

This example illustrates the use of 7.5 percent molar excess of 2,3,5,6-tetraminopyridine (TAP) in the making of monomer complex by a directly coupled process. A dipotassium salt of 2,5-dihydroxy terephthalic acid (K$_2$-DHTA/Na$_2$S$_2$O$_4$) solution was prepared in a vessel by combining 126.81 grams of K$_2$-DHTA, 2208 grams of water, and 2.2 grams sodium dithionate.

In an autoclave, 100.3 grams of 2,6-diamino-3,5-dinitro-pyridine (DADNP), 508 grams water, 2.04 gram 5% Pt/C catalyst (using 1 gram of catalyst per dry basis) and 10 grams of ammonium hydroxide were combined and heated to 65° C. at 500 psig. Hydrogenation of the DADNP was complete in 2 hours. After venting and cooling to 30° C., about 15 g of Darco G60 activated carbon in 100 g water was added as a slurry to the clave and mixed for 1 hour. The solution was filtered to remove the catalyst followed by a single CUNO Biocap 30 54SP filter. The filtration took 30 minutes and the color of the filtered solution was clear throughout the transfer.

The colorless TAP solution was added to the K$_2$-DHTA/Na$_2$S$_2$O$_4$ solution with mixing at 50° C. The color of the K$_2$-DHTA/Na$_2$S$_2$O$_4$ solution was light yellow and did not change during the TAP addition the pH of the TAP/K$_2$-DHTA mixture was 10.0. The clave and filters were then rinsed with 100 g H$_2$O which was added to the vessel. The theoretical amount of TAP, including DADNP purity (98%) that could have been made, filtered, and transferred to the mix vessel was 68.8 g (0.494 mol) giving a maximum TAP/K$_2$-DHTA molar ratio of 1.075.

A 150 ml of pre-mixed phosphate buffer solution (pH=4.7) was diluted with 600 ml water and precharged in a coupling vessel and heated to 50° C. while mixing. The basic TAP/K$_2$-DHTA mixture (pH=10) was added to the coupling vessel while simultaneously adding 25% aqueous H$_3$PO$_4$ to control the pH around 4.5. Large amounts of fine light-yellow monomer complex crystals formed almost immediately and increased during the addition. The final pH was brought to 4.5 while the monomer complex slurry cooled to 30° C. The slurry was filtered giving a pale yellow cake. The monomer complex cake was washed 3 times with 400 g each of water followed by 200 g of ethanol before being set to purge with nitrogen overnight. The color of the cake was pale yellow.

Example D

This example illustrates the effect of production of a monomer complex made with a 1:1 ratio of TAP and DHTA. The following were combined in a clean dry 2CV Model DIT Mixer (available from Design Integrated Technology, Inc, Warrenton, Va.) that was continuously purged with nitrogen gas:

a) 62.4 grams of polyphosphoric acid (PPA) with a concentration of 84.84% P$_2$O$_5$,
b) 14.71 grams of P$_2$O$_5$,
c) 0.11 grams of tin powder (325 mesh and available from VWR scientific; this amount is 0.5% based on weight of TD-complex or 0.01421 millimoles Tin/millimoles TD-complex), and
d) 22.89 grams of TD-Complex (a one to one complex of tetraminopyridine (TAP) and dihydroxyterephthalic acid, i.e., 47.21 g of TAP and 67.21 g of DHTA).

The CV Model was a jacketed twin cone reactor that was heated by the circulation of hot oil through the jacket. This reactor used intersecting dual helical-conical blades that intermesh throughout the conical envelope of the bowl. The mixer blades were started and set at about 53 rpm. The reactor was swept with dry N$_2$ gas. The temperature of the reaction mixture was measured throughout using a thermocouple. The temperature of the reaction mixture was raised to 100° C. and held for 1 hour. The temperature of the reaction mixture was raised to 137° C. and held for 3 hours. Next, the temperature of the reaction mixture was raised to 180° C. and held under vacuum for 3 hours. The mixer was purged with nitrogen and the polymer solution was discharged into a glass vessel. The polymer was removed from the mixer in the form of a solution in PPA. A sample of the polymer was separated from the solution and then diluted with methane sulfonic acid ("MSA") to a concentration of 0.05% polymer solids. The inherent viscosity of the polymer sample was 6 dl/g.

Metal Powder Examples. The following examples demonstrate the effectiveness of tin (Sn), vanadium (V), chromium (Cr) and iron (Fe) metals as reducing agents during polymerization.

Example 5

The following were combined in a clean dry 2CV Model DIT Mixer that was continuously purged with nitrogen gas:
a) 126.5 grams of polyphosphoric acid (PPA) with a concentration of 85.15% $P_2O_5$,
b) 26.82 grams of $P_2O_5$,
c) 0.23 grams of tin powder (325 mesh and available from VWR scientific; this amount is 0.5% based on weight of TD-complex or 0.01421 millimoles Tin/millimoles TD-complex), and
d) 45.78 grams of TD-Complex (a one to one complex of Tetraminopyridine (TAP) and dihydroxyterephthalic acid, i.e. effectively 94.42 g of TAP and 134.42 g of DHTA, an approximately 10% molar excess of TAP used during preparation).

A CV Model oil heated twin cone reactor having intersecting dual helical-conical blades that intermesh throughout the conical envelope of the bowl was used. The mixer blades were started and set at 53 rpm and a vacuum was pulled on the reaction mixture in such a way as to moderate the foaming of the mixture during the reaction. The temperature of the reaction mixture was measured throughout using a thermocouple. The temperature was raised to 100° C. and held for 1 hour. The temperature was raised to 137° C. and held for 3 hours. Next the temperature was raised to 180° C. and held under vacuum for 3 hours. The mixer was purged with nitrogen and the polymer solution was discharged into a glass vessel. The polymer was removed from the mixer in the form of an a solution in PPA.

A sample of the resulting polymer solution was diluted in methane sulfonic acid (MSA) at a concentration of 0.05% polymer solids. The inherent viscosity of the polymer sample produced was 23 dl/g. See Table 1.

Example 6

The procedure of Example 5 was repeated using 0.01421 millimoles of iron powder/millimoles TD-complex. The inherent viscosity of the polymer sample produced was measured as 29 dl/g. See Table 1.

Example 7

The procedure of Example 5 was repeated using 0.01421 millimoles of vanadium and chromium powder/millimoles TD-complex. The inherent viscosities of the polymer samples produced were both 22 dl/g using vanadium and chromium. See Table 1.

Example B

Example 5 was repeated without reducing metal. The resulting inherent viscosity was 9 dl/g. See Table 1

Example C

Example 5 was repeated with the reducing metals copper (Cu), nickel (Ni), manganese (Mn), boron (B), titanium (Ti), aluminum (Al), gallium (Ga), cobalt (Co) and zinc (Zn). The results are shown in Table 2.

Example D

Example 5 was repeated with the metal salts tin chloride and magnesium chloride used as the reducing agents instead of metal powder. The results are shown in Table 3.

TABLE 1

Preferred Metal Reducing Agents

| Item | % Final $P_2O_5$ | % Solids | Metal | Mw | % wt (Based on Monomer) | mmoles Metal/mmole Polymer | Inherent Viscosity (dl/g) |
|---|---|---|---|---|---|---|---|
| Example B | 82.5 | 18 | None | | | | 9 |
| Example 5 | 82.5 | 18 | Sn | 118.7 | 0.500 | 0.01421 | 23 |
| Example 6 | 82.5 | 18 | Fe | 55.8 | 0.235 | 0.01421 | 29 |
| Example 7 | 82.5 | 18 | V | 50.94 | 0.215 | 0.01421 | 22 |
| Example 7 | 82.5 | 18 | Cr | 51.996 | 0.219 | 0.01421 | 22 |

TABLE 2

Evaluation of Metal Reducing Agents

| Polymerization | % Final $P_2O_5$ | % Solids | Metal | Mw | % wt (Based on Monomer)* | mmoles Metal/mmole Polymer | Inherent Viscosity (dl/g) |
|---|---|---|---|---|---|---|---|
| Example C | 82.5 | 18 | Cu | 63.5 | 0.268 | 0.01421 | 15 |
| Example C | 82.5 | 18 | Ni | 58.7 | 0.247 | 0.01421 | 16 |
| Example C | 82.5 | 18 | Mn | 54.9 | 0.231 | 0.01421 | 18 |
| Example C | 82.5 | 18 | B | 10.81 | 0.046 | 0.01421 | 17 |
| Example C | 82.5 | 18 | Ti | 47.88 | 0.202 | 0.01421 | 16 |
| Example C | 82.5 | 18 | Zn | 65.38 | 0.275 | 0.01421 | 17 |
| Example C | 82.5 | 18 | Al | 26.98 | 0.114 | 0.01421 | 17 |
| Example C | 82.5 | 18 | Ga | 69.72 | 0.294 | 0.01421 | 18 |
| Example C | 82.5 | 18 | Co | 58.93 | 0.248 | 0.01421 | 16 |

TABLE 3

Evaluation of Metal Salt Reducing Agents

| Polymerization | % Final P$_2$O$_5$ | % Solids | Metal | Mw | % wt (Based on Monomer)* | mmoles Metal Salt/mmole Polymer | Inherent Viscosity (dl/g) |
|---|---|---|---|---|---|---|---|
| Example D | 82.5 | 18 | SnCl$_2$(H$_2$O)$_2$ | 225.63 | 0.951 | 0.01421 | 20 |
| Example D | 82.5 | 18 | MgCl$_2$ | 95.23 | 0.401 | 0.01421 | 19 |

Example 8

Optimization of Reducing Agent During Polymerization. The following were combined in a clean dry 4CV Model DIT Mixer that was continuously purged with nitrogen gas:

a) 643.94 grams of polyphosphoric acid (PPA) having a concentration of 84.79% P$_2$O$_5$,
b) 127.22 grams P$_2$O$_5$,
c) 2.5 grams of tin powder (325 mesh and available from VWR scientific; this amount of tin powder is approximately 1.09 weight percent based on the amount of TD Complex), and
d) 228.84 grams of TD Complex (a one to one complex of tetraminopyridine (TAP) and dihydroxyterephthalic acid, i.e., effectively 94.42 g of TAP and 134.42 g of DHTA, an approximately 10% molar excess of TAP used during preparation).

The CV Model was a oil-heated twin cone reactor that used intersecting dual helical-conical blades that intermesh throughout the conical envelope of the bowl. The mixer blades were started and set at 53 rpm and a vacuum was pulled on the reaction mixture in such a way as to moderate the foaming of the mixture during the reaction. The temperature of the reaction mixture was measured using a thermocouple. The temperature was raised to 100° C. and held for 1 hour. The temperature was raised to 135° C. and held for 3 hours. Next the temperature was raised to 180° C. and held for 2 hours. The mixer was purged with nitrogen and the polymer solution was discharged into a glass vessel. The polymer was removed from the mixer in the form of a solution in PPA.

Figure 2:
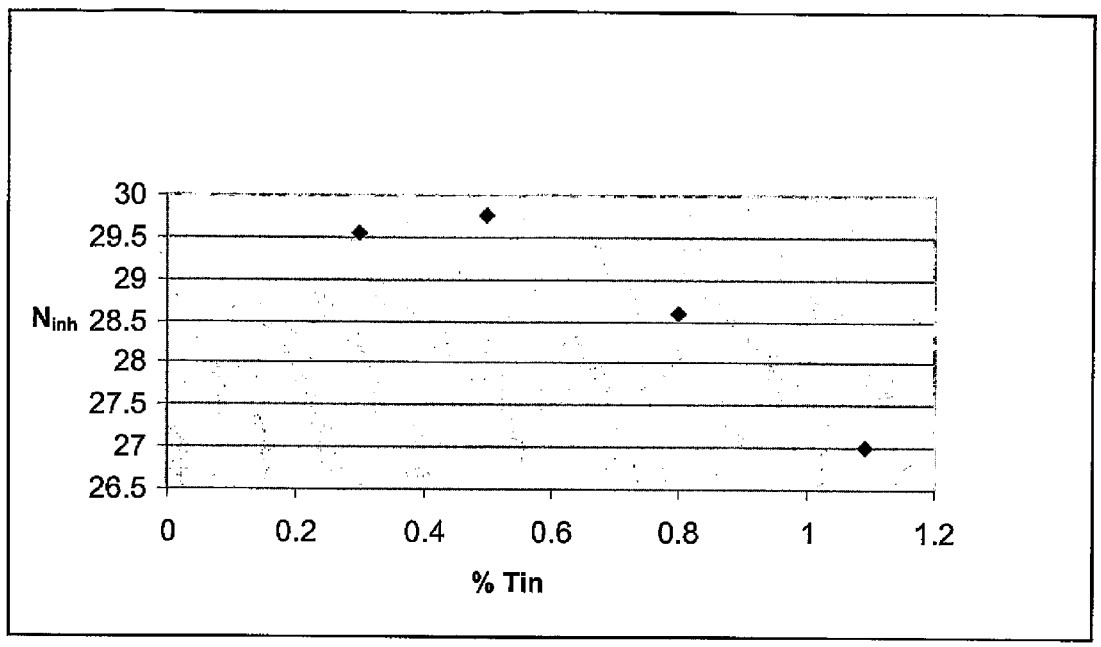
FIG. 2 is a graphical representation of inherent viscosity versus tin content of polyareneazole polymer solutions according to certain embodiments of the present invention that are listed in Table 4.

A sample of the resulting polymer solution was diluted in methane sulfonic acid (MSA) at a concentration of 0.05% polymer solids. The inherent viscosity of this sample was measured as 27 dl/g and was designated Item 1 in Table 4. This procedure was repeated using 0.8, 0.5, 0.3, 0.074 and 0% tin based on the weight of TD Complex used. The trend of inherent viscosity versus tin content is shown graphically in FIG. 2.

TABLE 4

| Item | Polymer Solids | % Final P$_2$O$_5$ | % Tin Powder* | Inherent Viscosity (dl/g) |
|---|---|---|---|---|
| 1 | 18 | 82.1 | 1.09 | 27 |
| 2 | 18 | 82.1 | 0.8 | 28.6 |
| 3 | 18 | 82.1 | 0.5 | 29.8 |
| 4 | 18 | 82.1 | 0.3 | 29.6 |
| 5 | 18 | 82.1 | 0.074 | 17.5 |
| 6 | 18 | 82.1 | 0 | 6.9 |

*As a percentage of wt TD Complex used.

Fiber Spinning Examples

Example 9

Polymerization with Sn (10% molar excess TAP with spun fiber). The following were combined in a clean dry 4CV Model DIT Mixer that was continuously purged with nitrogen gas:

a) 663.0 grams of polyphosphoric acid (PPA) having a concentration of 85.15% P$_2$O$_5$,
b) 112.5 grams P$_2$O$_5$,
c) 1.1 grams of tin powder (325 mesh and available from VWR scientific; This amount of Tin powder is approximately 0.5% weight percent based on the amount of TD Complex), and
d) 230.0 grams of TD Complex (a one to one complex of Tetraminopyridine (TAP) and dihydroxyterephthalic acid, i.e. 94.45 g of TAP and 134.45 g of DHTA).

The 4CV Model was a jacketed twin cone reactor, which was heated by hot oil circulating through the jacket, that used intersecting dual helical-conical blades that intermesh throughout the conical envelope of the bowl. The mixer blades were set at 80 rpm and a vacuum was pulled on the reaction mixture in such a way as to moderate the foaming of the mixture during the reaction. The temperature of the reaction mixture was measured using a thermocouple. The temperature of the reaction mixture was raised to 100° C. and held for 1 hour. The temperature was raised to 135° C. and held for 4 hours. Next the temperature was raised to 180° C. and held for 2 hours. The mixer was purged with nitrogen and the polymer solution was discharged into a glass vessel. The polymer was removed from the mixer in the form of a solution in PPA. A sample of the polymer solution was diluted with methane sulfonic acid to 0.05% concentration. The resulting polymer had an inherent viscosity of 26 dl/g.

Fiber Spinning. The polymerized polymer solution in polyphosphoric acid, was spun into a multifilament yarn through a 250 hole spinneret having 90 micron diameter holes using a dry-jet-wet spinning technique, with water being used as the coagulation medium. The air-gap length was 15 mm, the spin draw ratio in the air-gap was approximately 14. The bobbin of multifilament yarn was washed in hot (50 C) water for two weeks prior to being dried. The wet yarn was dried at 170 C under a tension of 890 g by passing it through a four-section, 170-inch long tube oven purged with nitrogen at a speed of 7 m/min. The resulting 373 denier yarn had the following physical properties: tenacity/elongation/modulus 27.8 gpd/2.62%/1345 gpd.

Example 10

Polymerization with Fe Metal (10% molar excess TAP with spun fiber). The following were combined in a clean dry 4CV Model DIT Mixer that was continuously purged with nitrogen gas:

a) 682.1 grams of polyphosphoric acid (PPA) having a concentration of 85.65% $P_2O_5$,
b) 89 grams $P_2O_5$,
c) 1.15 grams of iron powder (325 mesh and available from Sigma-Aldrich; This amount of Fe powder is approximately 0.5% weight percent based on the amount of TD Complex), and
d) 228.9 grams of TD Complex (a one to one complex of Tetraminopyridine (TAP) and dihydroxyterephthalic acid, i.e. 94.45 g of TAP and 134.45 g of DHTA).

The 4CV Model was heated by hot oil and used intersecting dual helical-conical blades that intermeshed throughout the conical envelope of the bowl. The mixer blades were started and set at 80 rpm and a vacuum was pulled on the reaction mixture in such a way as to moderate the foaming of the mixture during the reaction. The temperature of the reaction mixture is measured throughout using a thermocouple. The temperature of the reaction mixture was raised to 100° C. and held there for 1 hour. The temperature was raised to 135° C. and held for 4 hours. Next the temperature was raised to 180° C. and held for 2 hours. The mixer was purged with nitrogen and the polymer solution was discharged into a glass vessel. The polymer was removed from the mixer in the form of a solution in PPA. A sample of the polymer solution was diluted with methane sulfonic acid to 0.05% concentration. The $n_{inh}$ was 24 dl/g.

Fiber Spinning. The polymerized polymer solution in polyphosphoric acid, was spun into a multifilament yarn through a 250 hole spinneret having 90 micron diameter holes using a dry-jet-wet spinning technique, with water being used as the coagulation medium. The air-gap length was 20 mm, the spin draw ratio in the air-gap was approximately 14. The bobbin of multifilament yarn was washed in boiling water for 90 minutes, followed by soaking in 2 wt % aqueous caustic for 2 hours, followed by soaking in water for 2 hours, the water being exchanged for fresh water twice, followed by soaking in 2 wt % aqueous acetic acid for 2 hours, followed by soaking in fresh water for 2 hours, the water being exchanged for fresh water twice. The bobbin of washed yarn was stored wet in a plastic bag until dried in a tube oven. The yarn was dried at 170 C under a tension of 1000 grams by passing it through a 1-foot long tube oven purged with nitrogen at a speed of 0.5 m/min. The resulting 387 denier yarn had the following physical properties: tenacity/elongation/modulus 25.9 gpd/ 2.24%/1398 gpd.

What is claimed is:

1. A process for making a polyareneazole comprising:
    contacting a molar excess in a ratio of at least 1.05 to 1 of a 2,3,5,6-tetraaminopyridine free base in water with a 2,5-dihydroxy terephthalic acid salt to form an aqueous mixture,
    adjusting the pH of the aqueous mixture to within the range of from about 3 to about 5 to precipitate a monomer complex, and
    polymerizing the monomer complex to form a polyareneazole having an inherent viscosity of at least about 25 dl/g at 30° C. at a polymer concentration of 0.05 g/dl in methane sulfonic acid.

2. The process of claim 1 wherein the molar ratio is in excess of about 1.075 to 1.

3. The process of claim 2 wherein the molar ratio is in excess of about 1.15 to 1.

4. The process of claim 1 wherein the pH is adjusted by adding orthophosphoric acid to the aqueous mixture.

5. The process of claim 1, wherein the 2,5-dihydroxy terephthalic acid salt is an alkaline salt or an ammonium salt of 2,5-dihydroxy terephthalic acid.

6. The process of claim 5, wherein the alkaline salt is 2,5-dihydroxy terephthalic acid dipotassium salt.

7. The process of claim 1, wherein the pH of the aqueous mixture is adjusted to within the range of from about 4.3 to about 4.6 to precipitate the monomer complex.

8. The process of claim 1, wherein the polyareneazole is poly(1,4-(2,5-dihydroxy)phenylene-2,6-pyrido[2,3-d:5,6-d'] bisimidazole).

9. A process for making a monomer complex comprising:
    contacting 2,3,5,6-tetraminopyridine free base in water with 2,5-dihydroxy terephthalic acid dipotassium salt to form an aqueous mixture, and
    adjusting the pH of the aqueous mixture to within the range of from about 3 to about 5 to precipitate the monomer complex,
    wherein the molar ratio of the 2,3,5,6-tetraminopyridine free base to the 2,5-dihydroxy terephthalic acid dipotassium salt is in excess of about 1.05 to 1.

10. The process of claim 9 wherein the molar ratio is in excess of about 1.075 to 1.

11. The process of claim 10 wherein the molar ratio is in excess of about 1.15 to 1.

12. The process of claim 9 wherein the pH is adjusted by adding dilute orthophosphoric acid to the aqueous mixture.

13. The process of claim 9, wherein the pH of the aqueous mixture is adjusted to within a range of from about 4.3 to about 4.6 to precipitate the monomer complex.

* * * * *